(12) United States Patent
Wilke

(10) Patent No.: US 8,662,818 B2
(45) Date of Patent: Mar. 4, 2014

(54) APPARATUS AND METHOD FOR TURNING RACKS

(75) Inventor: Christian Wilke, Rimbach (DE)

(73) Assignee: LEICA Biosystems Nussloch GmbH, Nussloch (DE)

( * ) Notice: Subject to any disclaimer, the term of this patent is extended or adjusted under 35 U.S.C. 154(b) by 15 days.

(21) Appl. No.: 13/316,602

(22) Filed: Dec. 12, 2011

(65) Prior Publication Data

US 2012/0148380 A1 Jun. 14, 2012

(30) Foreign Application Priority Data

Dec. 13, 2010 (DE) .......................... 10 2010 054 360

(51) Int. Cl.
*B65G 47/22* (2006.01)
*B65G 7/08* (2006.01)

(52) U.S. Cl.
USPC ............................ 414/754; 414/758; 414/768

(58) Field of Classification Search
USPC ......... 414/754, 758, 768, 769, 772, 776, 777, 414/779, 936, 940
See application file for complete search history.

(56) References Cited

U.S. PATENT DOCUMENTS

| | | | | |
|---|---|---|---|---|
| 3,930,643 A * | 1/1976 | Moore | ............................ | 269/58 |
| 4,129,093 A | 12/1978 | Johnson | | |
| 4,322,198 A * | 3/1982 | Zuber | ........................... | 414/754 |
| 5,507,614 A * | 4/1996 | Leonov et al. | ................. | 414/768 |
| 5,641,265 A * | 6/1997 | Spada et al. | .................... | 414/779 |
| 6,745,916 B2 * | 6/2004 | Plank et al. | ........................ | 221/1 |
| 7,153,474 B2 | 12/2006 | Thiem | | |
| 2002/0051735 A1 | 5/2002 | Dorenkamp et al. | | |
| 2005/0002765 A1 * | 1/2005 | Lambright | .................... | 414/466 |
| 2005/0064535 A1 | 3/2005 | Favuzzi et al. | | |
| 2008/0014119 A1 | 1/2008 | Metzner | | |
| 2009/0155907 A1 | 6/2009 | Winther et al. | | |
| 2010/0311108 A1 | 12/2010 | Bishop et al. | | |
| 2011/0136135 A1 | 6/2011 | Larsen et al. | | |

FOREIGN PATENT DOCUMENTS

| | | |
|---|---|---|
| GB | 2429775 A | 3/2007 |
| WO | 95/20176 A1 | 7/1995 |

* cited by examiner

*Primary Examiner* — Gregory Adams
*Assistant Examiner* — Lynn Schwenning
(74) *Attorney, Agent, or Firm* — Hodgson Russ LLP

(57) ABSTRACT

The invention relates to apparatuses for turning racks (1) for specimen slides (4), having a rack receptacle for at least one rack, the rack (1) being oriented in the rack receptacle horizontally in a first position such that specimen slides in the rack are arranged vertically next to one another relative to a longitudinal axis of the rack, and the rack receptacle being pivotable around a rotation axis (8) into a second position in which the rack (1) is oriented vertically. The rotation axis (8) of the rack (1) extends obliquely with respect to the longitudinal axis (5) of the horizontally oriented rack (1), so that the rack (1) can be pivoted back and forth between the first and the second position by means of a 180-degree rotation around the rotation axis (8).

15 Claims, 4 Drawing Sheets

Fig. 3
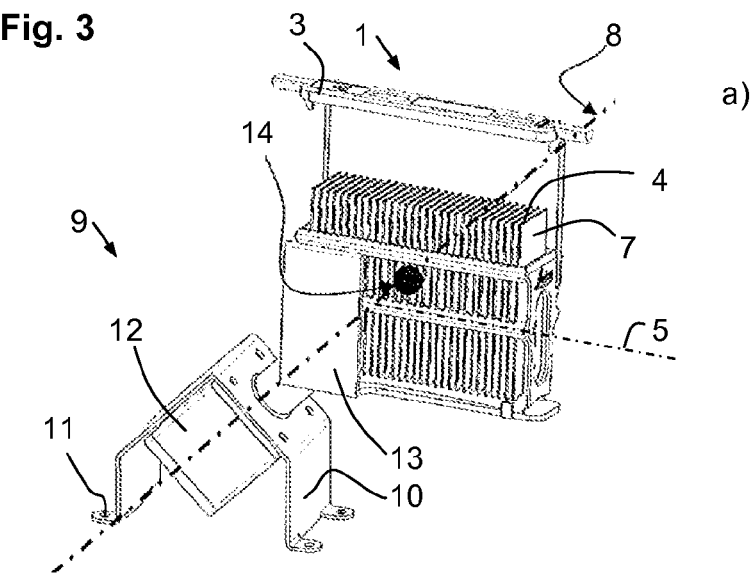
a)
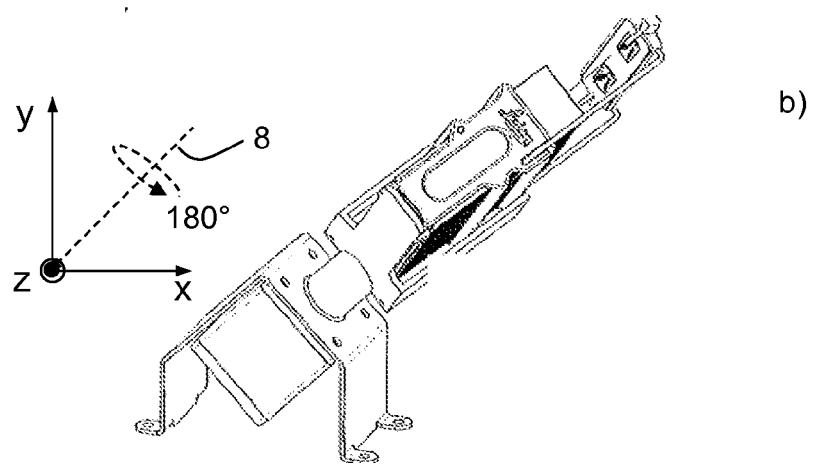
b)
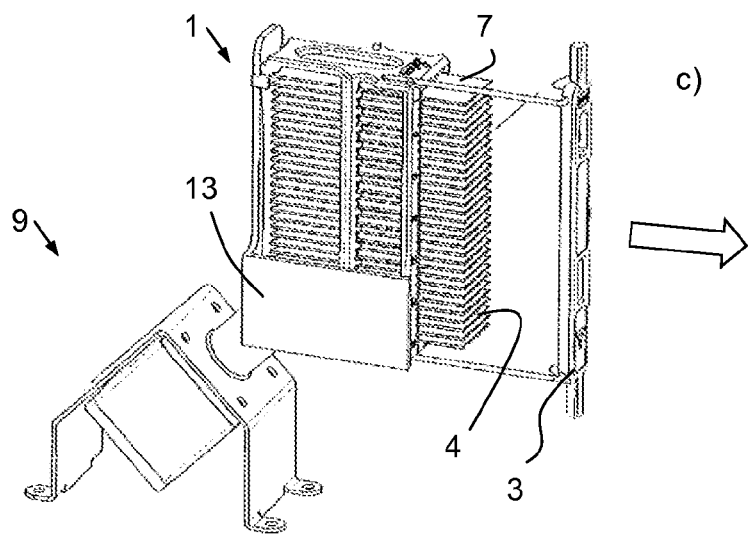
c)

APPARATUS AND METHOD FOR TURNING RACKS

CROSS REFERENCE TO RELATED APPLICATIONS

This application claims priority of German patent application number 10 2010 054 360.8 filed Dec. 13, 2010, the entire disclosure of which is incorporated by reference herein.

FIELD OF THE INVENTION

The invention relates to an apparatus for turning racks ("rack turners") for specimen slides, for use in systems for preparing tissue samples for histological investigations, having a rack receptacle, wherein the longitudinal axis of the rack disposed in said rack receptacle is oriented horizontally in a first position and the specimen slides are arranged vertically next to one another relative to said longitudinal axis of the rack, and wherein the rack receptacle is pivotable around a rotation axis into a second position in which the rack is oriented vertically; and to a method for turning racks between the first and the second position.

BACKGROUND OF THE INVENTION

Apparatuses of this kind are used in particular in systems in which stained specimens or tissue samples, such as a histological section, on specimen slides are provided with a coverslip in order to be analyzed later under a microscope. Staining of the specimens takes place in stainers, in which the specimen slides having the tissue samples are sorted into racks or specimen slide holders and, together with them, immersed into stain containers. During this process, the specimen slides are arranged vertically next to one another in the horizontally oriented rack. The racks used are principally ones in which a rack basket is suspended from a pivotable bail at which the rack can be grasped and transported. This bail also serves as a closure mechanism that prevents unintentional removal of the specimen slides from the rack. After staining, the rack is transferred to a coverslipper, where the coverslipping process takes place.

In stainers as well as in coverslippers, racks are used for storing specimens. In the stainer, the specimen slides are arranged vertically in the rack in order to enable the staining medium to run off the specimen slide in the best possible way. In the coverslipper, the specimen slides are oriented horizontally in order to prevent the coverslipping medium from flowing off the specimen slide. The specimen is oriented upward in that position. In both apparatuses (stainer and coverslipper), the racks are introduced into the respective apparatus through a drawer. During placement of the rack, the orientation of the racks must be identical. Thereby, incorrect positioning by the user is avoided. In addition, there is the need for the specimen to be accessible for the user in case of a failure of the staining process.

Prior to coverslipping, the specimen slides are as a rule first introduced into input cuvettes with solvent (xylene) in order to ensure better flow characteristics for the coverslipping agent used during coverslipping. The rack having the specimen slides is then conveyed to a coverslipping unit where firstly the coverslipping medium (an adhesive or the like) is applied onto the specimen slides, and then the coverslip is put in place to seal off the tissue sample. In order to achieve a maximally optimal process result, the specimen slides must remain vertical in the rack for a long time after staining. At the same time, the coverslipping process demands that the specimen slide be oriented horizontally in order to prevent the coverslipping medium from running off the specimen slide. This requires that the specimen slide be reoriented before coverslipping.

This can be accomplished by pivoting the entire rack 90 degrees from a horizontal position into a vertical position, with the result that the specimen slides, arranged perpendicularly relative to the longitudinal axis of the rack, become horizontally oriented (so-called "rack processing"). The specimen slides are then removed from the rack, and the process of coverslipping the individual specimen slides can begin. Certain coverslipping methods require that the sample on the specimen be oriented upward. In addition, the rack must also be oriented so that the specimen slides can be removed from the rack. An incorrectly inserted rack can mean that the wrong side of the rack is oriented toward the coverslipping unit, and that the coverslipping process cannot begin.

A processing machine, known from WO 95/20176, for applying coverslips onto specimen slides provides a receptacle, serving as an input door, into which a rack having vertically inserted specimen slides can be slid. The receptacle is then swung from an initially horizontal position into a vertical position. A gripper grasps the now horizontally oriented specimen slides, pulls them individually out of the rack, and conveys them to a coverslipping apparatus or unit. A possibility that cannot be precluded, however, is that the rack becomes inserted into the receptacle the wrong way around in the context of rack processing, and that after the rack is brought upright, the sample is arranged on the wrong side of the specimen slide. The rack would then need to be reoriented.

A high level of process reliability must be guaranteed in fully automatic stainers and coverslippers, but also in the context of combination devices such as those known, for example, from DE 101 44 989 B4. This means that the racks are delivered to the coverslipping unit in a correct orientation even if the machines are incorrectly loaded. The tissue sample must be located on the upper side of the specimen slide, and the rack must be correctly oriented. If the incorrect orientation of a rack is not detected and corrected, in the worst case the process must be interrupted and the placement of the rack must be corrected by a laboratory worker. Automatic correction mechanisms are therefore desirable.

DE 100 41 230 A1 discloses a transport device having a robot arm having an end-located gripper that can grasp the racks and lift them along a vertical axis. The transport device is made up of multiple sub-arms, and can rotate and reorient the racks around the vertical axis. This apparatus cannot, however, swing the rack.

SUMMARY OF THE INVENTION

It is therefore an object of the invention to propose a simple and time-saving capability for reorienting the racks. The outlay for reorienting the rack should also be as small as possible in terms of the complexity of the system as a whole.

This object is achieved according to the present invention in that the rotation axis of the rack extends obliquely with respect to the longitudinal axis of the horizontally oriented rack, so that the rack can be pivoted back and forth between the first and the second position by means of a 180-degree rotation around the rotation axis. This enables an easy automatic reorientation of the rack from the horizontal into the vertical position, two motions around two axes being combined into one motion around one axis. The first axis concerns the orientation from horizontal to vertical, the specimen not being accessible for the user at this state. The second axis concerns the rotation of the rack by 180°, by what the specimen become accessible for the user. As merely one axis of movement is necessary within the coverslipper, construction of the system is simplified. The racks can be introduced into the system in a coverslipper as well as in a stainer.

From US 2005/0064535 A1, staining apparatuses are known wherein several slides are received in receiving compartments lying next each other. A similar construction shows the apparatus for automatic removal of an embedding medium described in US 2009/0155907 A1. In each case, the racks are designed in such way that the longitudinal sides of the slides are arranged parallel to each other. As a result, there is free access to the surface of the individual slide. The receiving compartments are equipped with pivotable holder clips for keeping the slides in the respective position by means of a clamping. The holder clips are individually pivotable with respect to the rack between a horizontal and a vertical position. Such rack arrangements, however, are not faced with the problem that the specimen slides can fall out of the rack or experience uncontrolled movement when the rack is turned. The rack according to the invention, however, is a rack for receiving specimen slides, wherein the respective surfaces of the slides are arranged in a parallel relationship. Accordingly, the slides are not accessible is this state. Since the specimen slides are not fixed in the rack, there is always the danger that the specimen slides fall out of the rack when the rack is turned.

DE 10 2005 042 214 A1 describes a receiving and transferring station for coverslipped specimen slides lying horizontally oriented in magazine frames. The magazine frames are arranged on a rotation apparatus and can be conveyed from a receiving position into a transferring position by said rotation. Turning or tilting of the magazine frame is, however, not possible.

In US 2010/0311108 A1, a system is disclosed for agitating multiple specimen containers, said containers being received in a plurality of racks. The containers are transferred to the system in an upright standing position to be picked-up in the entrance location by a multiaxial working robotic transfer arm afterwards. Then, the containers are transferred to receiving structures. Afterwards, they are pivoted in a horizontal position and loaded into said structures. The rack is then rotationally moved or agitated.

The turning/tilting device according to the invention for racks with specimen slides accommodated therein, ensures that the specimen slides disposed in the rack are moved from a vertical to a horizontal position, thereby keeping the specimen slides from falling out of the rack or from moving uncontrollably when the rack is turned. This would be the case when the rack is merely tilted by 90°.

The rack turner according to the invention can be used in both stainers and coverslippers. For example, if a rack is introduced the wrong way around into the system by the laboratory worker on duty, the incorrect positioning can be corrected. A corresponding transport apparatus can check the orientation of the rack and authorize a reorientation. Stainers and coverslippers can be made more reliable in terms of processing, such that a simple apparatus corrects human errors.

According to a preferred embodiment of the invention, the rotation axis of the rack is inclined 45 degrees with respect to the longitudinal axis of the horizontally oriented rack. When the rotation axis in further development of the invention's concept extends through the physical center of gravity of the rack, only a small drive force is sufficient for the rotary motion. The result of turning at the center of gravity is that no tilting moments occur, making the turning operation particularly reliable and low-load.

According to a further advantageous embodiment of the invention, at least one sensor is provided for sensing the rotary motion of the rack receptacle around the rotation axis. A sensor apparatus of this kind contributes considerably to process reliability.

The invention further encompasses a rack turning module having the rack turner according to the present invention, the rack receptacle being connected rotatably to a base element, and the base element comprising a drive system for rotating the rack receptacle around the rotation axis. As an independent and separately installable element for stainers or coverslippers, the module represents a simple and economical solution to human or technological errors, so that complex turning and pivoting systems can be omitted.

The invention furthermore relates to a method for turning racks for specimen slides, for use in systems for preparing tissue samples for histological investigations, the rack being pivoted between a first position in which the longitudinal axis of the rack extends horizontally and in which that specimen slides in the rack are arranged vertically next to one another relative to the longitudinal axis of the rack, and a second position in which the longitudinal axis of the rack extends vertically. Known turning or pivoting mechanisms merely provide for pivoting or turning the rack around only one axis in each case, the axis extending either parallel or perpendicular to the longitudinal axis of the rack. In accordance with the method according to the present invention, for swinging from the first into the second position or from the second into the first position, the rack is swung 180 degrees around a rotation axis that extends obliquely with respect to the longitudinal axis of the horizontally oriented rack. The result is not only that two rotary motions are combined into one rotary motion, but that the energy expenditure for reorienting the rack is reduced to a minimum.

BRIEF DESCRIPTION OF THE DRAWING VIEWS

The invention will be further explained below with reference to exemplifying embodiments that are depicted in the drawings. All the features described and/or graphically depicted, individually or in any combination, constitute the subject matter of the invention regardless of their grouping in the Claims or the references thereof.

In the drawings:

FIG. 3 is a perspective view of the rack turner according to the present invention.

DETAILED DESCRIPTION OF THE INVENTION

Figure 1:
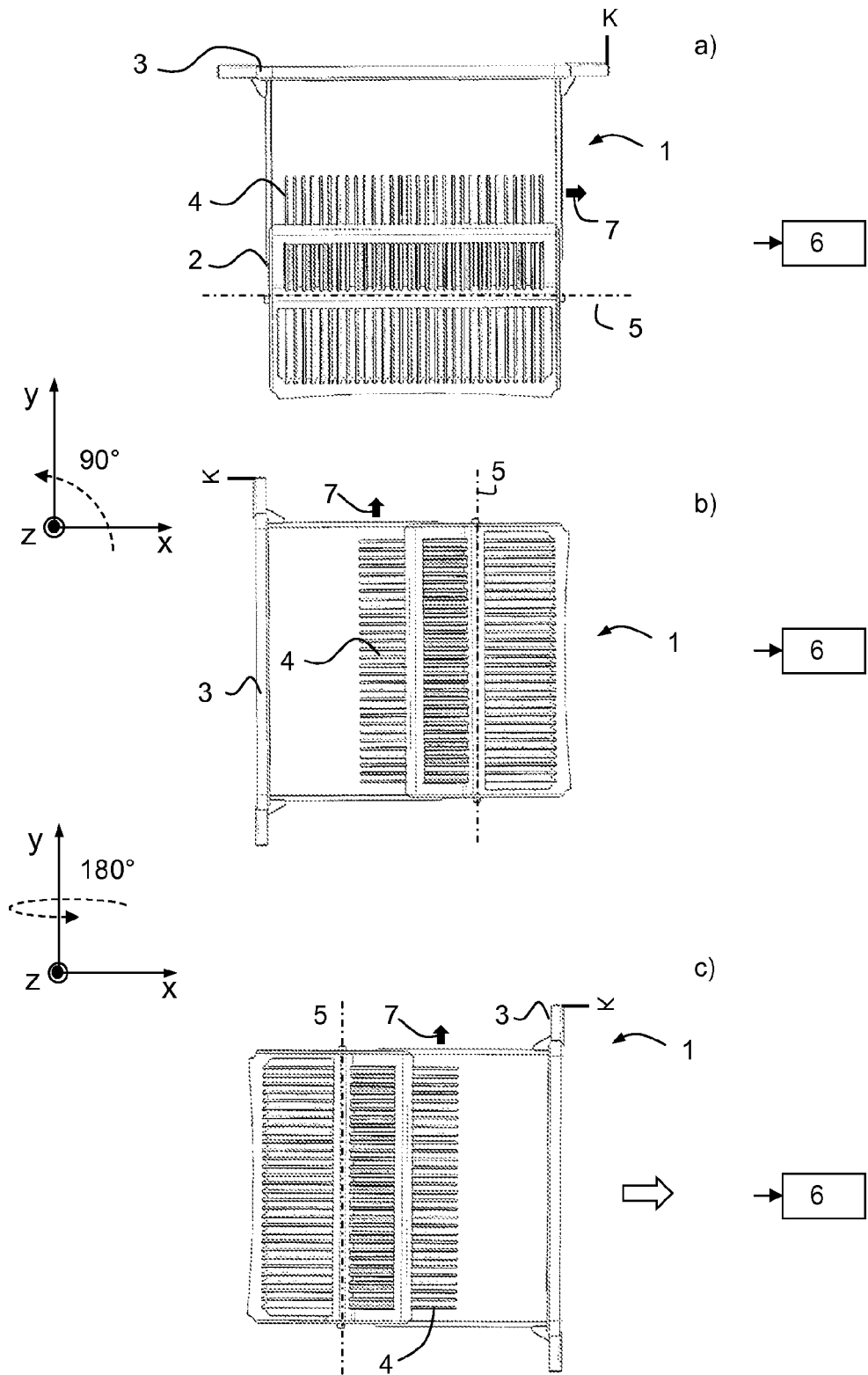
FIG. 1 shows the manner of operation of a known rack turner.

FIG. 1 shows a rack 1, used in stainers and coverslippers, in a variety of orientations *a*), *b*), and *c*). Rack 1 is made up substantially of a rack basket 2 and a rack bail 3, rack basket 2 being suspended from rack bail 3. A plurality of specimen slides 4 are inserted vertically in rack basket 2. Longitudinal axis 5 of rack basket 2 is oriented vertically. It is with rack 1 in this position that, inter alia, the staining process (in which rack 1 is immersed into stain containers) is carried out. The vertical position of specimen slides 4 is relevant for the subsequent coverslipping process, since it enables optimum run-off of the staining agent.

Shown in the Figure to the right of rack 1 is a black box 6 representing a coverslipping unit. Instead of a coverslipping unit, black box 6 can also stand for another processing station that requires a specific orientation of the rack. For the coverslipping process, specimen slides 4 must be removed from rack 1 and delivered to coverslipping unit 6. It is necessary to orient specimen slides 4 horizontally in order to prevent run-off of a coverslipping medium applied onto the specimen slides, and the tissue sample must be arranged on the upper side of specimen slides 4. At the same time, rack 1 must also be aligned so that specimen slides 4 can be removed from the rack in the direction of coverslipping unit 6. Only then can specimen slide 4 be delivered into coverslipping unit 6.

Specimen slides 4 can be removed from rack 1 in only one direction, namely upward in illustration a); rack bail 3 shown here can be swung away to enable specimen slides 4 to be pulled or slid out of rack basket 2. An arrow labeled 7 marks the upper side of specimen slide 4, which in illustration a) is oriented toward coverslipping unit 6. In order to make rack 1 available to coverslipping unit 6, proceeding from illustration a) the possibility firstly exists of tilting the rack that is depicted 90 degrees clockwise. Arrow 7 would then, however, point downward, meaning that specimen slides 4 are incorrectly oriented for coverslipping unit 6. It is therefore necessary to reorient the rack before the coverslipping process begins. This can occur by way of two rotations around two axes, as elucidated by sections b) and c). The reference point (marked "K") at the upper right edge of rack bail 3 serves to illustrate the pivoting motions.

In illustration b), the rack is first tilted 90 degrees counterclockwise around the Z axis, with the result that upper side 7 of specimen slides 4 is oriented upward. Specimen slides 4 are thus oriented horizontally, but they cannot be removed to the right from rack 1. A further 180-degree rotation around the Y axis is needed in order to orient the opening side of rack 1, which is located in the region of rack bail 3, toward coverslipping unit 6. The result of this additional rotation is shown in illustration c). The result of the two successively performed rotary motions of the rack, through 90 degrees and then through 180 degrees, is that specimen slides 4 are oriented horizontally with their upper sides toward the top, and that the removal direction for the specimen slides is oriented toward coverslipping unit 6, as illustrated by an arrow. Control point K is now located at the top right, and faces toward coverslipping unit 6. Rack bail 3 can now be swung aside, and specimen slides 4 can be removed from the rack and the coverslipping process can be initiated.

Figure 2:
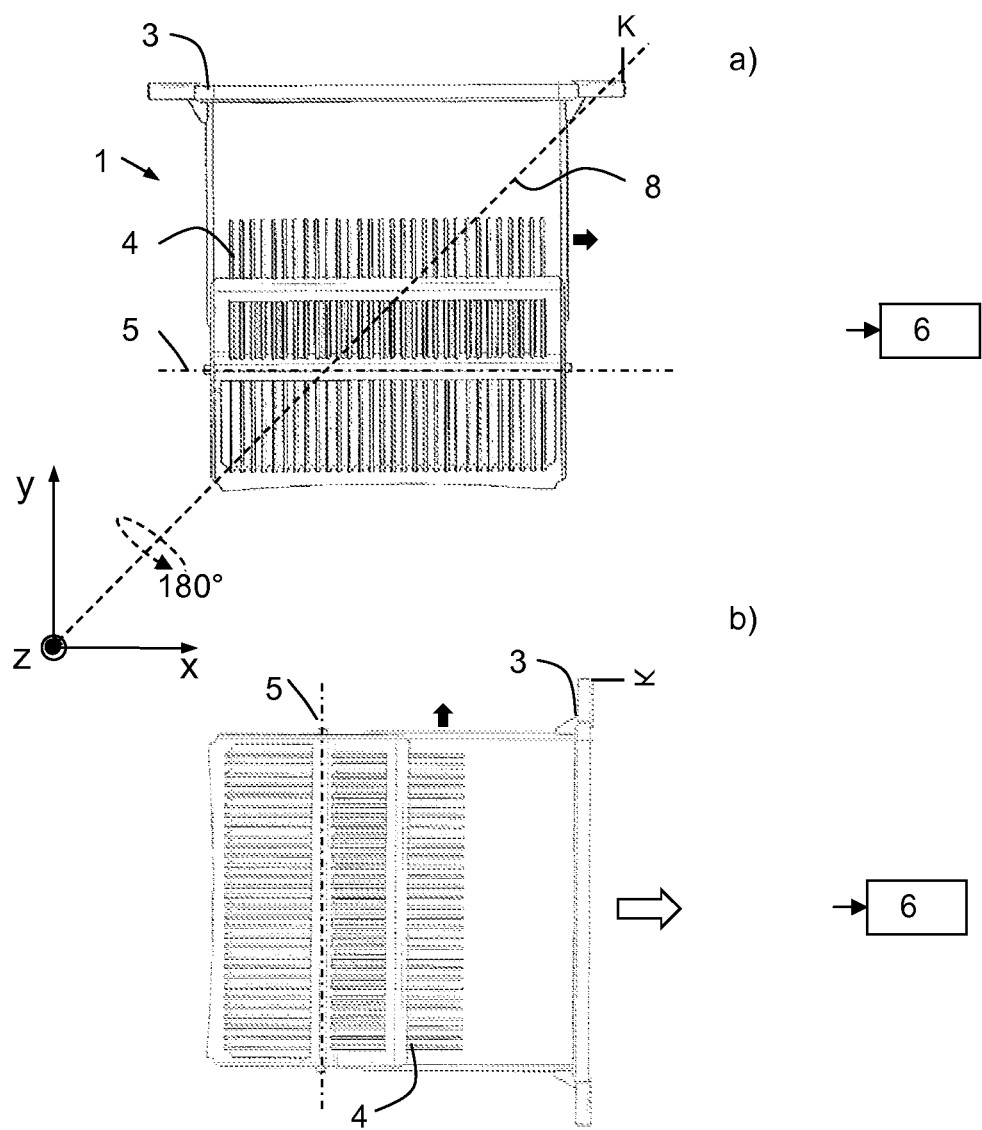
FIG. 2 shows the manner of operation of a rack turner according to the present invention.
Figure 4:
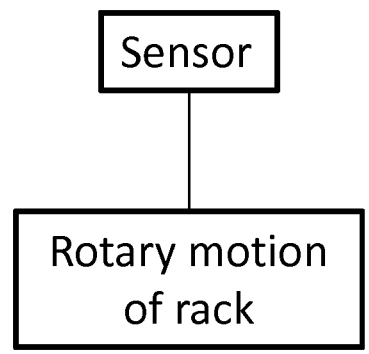
FIG. 4 is a schematic representation of a sensor arranged for sensing the rotary motion of the of the rack turner according to the present invention.

FIG. 2 shows, analogously to FIG. 1, a variety of orientations or process steps a) and b) of a rack reorientation, the reorientation of the rack occurring in accordance with the principle according to the invention. The plurality of rotary motions evident from FIG. 1 is not necessary in the context of the apparatus of FIG. 2.

FIG. 2 a) shows rack 1 in the same starting position as in FIG. 1 a). In FIG. 2 a), rack 1 is initially oriented so that a single 90-degree clockwise pivoting motion of the rack around the Z axis would cause the upper side of specimen slides 4 to be incorrectly oriented, i.e. to face downward. In order to orient rack 1 correctly for coverslipping unit 6, the rack must be reoriented as shown in FIG. 1. What serves as a rotation axis is a rotation axis 8 that, however, extends not perpendicularly but instead obliquely with respect to longitudinal axis 5 of the horizontally oriented rack 1. Rack 1 is rotated once through 180 degrees around this rotation axis 8, producing position b). Control point K has now, as shown in FIG. 1 c), assumed the final position that is correct for specimen slides 4, i.e. upper side 7 of specimen slides 4 is oriented upward, specimen slides 4 are arranged horizontally, and rack bail 3 is oriented toward coverslipping unit 6. Rack bail 3 can now be swung aside, and specimen slides 4 can be removed from rack 1 for the coverslipping process.

Whereas a reorientation of the rack in accordance with the process steps depicted in FIGS. 1 a) to c) requires a plurality of rotary motions, the reorientation principle according to the present invention considerably reduces the complexity and the motion energy required.

FIG. 3 shows a rack turner 9 in a variety of phases a), b), and c) of a pivoting operation for reorienting a rack. Rack turner 9 encompasses a base element 10 that possesses, in the lower region, mounting orifices 11 with which rack turner 9 can be installed in a coverslipper or stainer. A drive system 12 is provided on base element 10, which is connected to a receptacle 13 for a rack 1. Drive system 12 serves to rotate receptacle 13. Inserted into receptacle 13 is a rack 1 whose longitudinal axis extends, in the starting position depicted, horizontally. Specimen slides 4 are arranged vertically in rack 1, which means that rack 1 must first be reoriented before a coverslipping process begins. Drive system 12 serves to rotate receptacle 13 around rotation axis 8, which extends obliquely with respect to longitudinal axis 5 of the horizontally oriented rack 1. At the same time, rotation axis 8 extends through center of gravity 14 of rack 1. As illustrated by process step b), receptacle 13 is rotated 180 degrees around rotation axis 8 until it assumes the final position c). Rack bail 3 is now oriented toward the right, and upper side 7 of specimen slides 4 is at the top. Rack 1 is thus ready for the removal of specimen slides 4, which is depicted by an arrow. The coverslipping process can now begin immediately. Alternatively, a transport apparatus (not depicted) can be used to transport the rack to a coverslipping unit. Because rotation axis 8 extends through center of gravity 14 of rack 1, the energy needed for rotation of the rack is minimal.

PARTS LIST

1 Rack
2 Rack basket
3 Rack bail
4 Specimen slide
5 Longitudinal axis of rack
6 Coverslipping unit
7 Upper side of specimen slides
8 Rotation axis
9 Rack turner
10 Base element
11 Mounting orifice
12 Drive system
13 Receptacle
14 Center of gravity

What is claimed is:

1. An apparatus for turning racks (1) for specimen slides (4), for use in systems for preparing tissue samples for histological investigations, comprising:
   a rack (1) including a rack bail and a rack basket carrying specimen slides (4) suspended from the rack bail;
   a rack receptacle (13) configured to insertably receive a portion of the rack basket such that a longitudinal axis (5) of the rack (1) is disposed within said rack receptacle (13), the longitudinal axis (5) of the rack (1) being oriented horizontally in a first position and the specimen slides (4) in the rack (1) being arranged vertically next to one another relative to said longitudinal axis (5) of the rack (1), and the rack receptacle being pivotable around a rotation axis (8) into a second position in which the longitudinal axis (5) of the rack (1) is oriented vertically such that the specimen slides (4) are arranged horizontally next to one another relative to said longitudinal axis (5) and arranged such that the specimen slides (4) can be positioned to receive coverslips;

wherein the rotation axis (8) extends obliquely with respect to the longitudinal axis (5) of the horizontally oriented rack (1), so that, the rack (1) can be pivoted back and forth between the first and the second position by means of a 180-degree rotation around the rotation axis (8);

wherein in the first position, the specimen slides (4) are slidably removable vertically relative to the longitudinal axis (5), and in the second position, the specimen slides (4) are slidably removable in a horizontal direction relative to the longitudinal axis (5).

2. The rack turner according to claim 1, wherein the rotation axis (8) of the rack is inclined 45 degrees with respect to the longitudinal axis (5) of the rack (1).

3. The rack turner according to claim 1, wherein the rotation axis (8) extends through the physical center of gravity (14) of the rack.

4. The rack turner according to claim 1, further comprising at least one sensor arranged for sensing the rotary motion of the rack receptacle (13) around the rotation axis (8).

5. A rack turning module comprising:
a rack (1) including a rack bail and a rack basket carrying specimen slides (4) suspended from the rack bail;
a rack receptacle (13) configured to insertably receive a portion of the rack basket carrying specimen slides (4) such that a longitudinal axis (5) of the rack (1) is disposed within said rack receptacle (13), the longitudinal axis (5) of the rack (1) being oriented horizontally in a first position and the specimen slides (4) in the rack (1) are arranged vertically next to one another relative to said longitudinal axis (5) of the rack (1), and the rack receptacle is pivotable around a rotation axis (8) into a second position in which the longitudinal axis (5) of the rack (1) is oriented vertically such that the specimen slides (4) are arranged horizontally next to one another relative to said longitudinal axis (5) and arranged such that the specimen slides (4) can be positioned to receive coverslips, wherein the rotation axis (8) extends obliquely with respect to the longitudinal axis (5) of the horizontally oriented rack (1), so that, the rack (1) can be pivoted back and forth between the first and the second position by means of a 180-degree rotation around the rotation axis (8); and
a base element (10) including a drive system (12), wherein the rack receptacle (13) is connected rotatably to the base element (10), and the drive system (12) is operable to rotate the rack receptacle (13) around the rotation axis (8);
wherein in the first position, the specimen slides (4) are slidably removable vertically relative to the longitudinal axis (5), and in the second position, the specimen slides (4) are slidably removable in a horizontal direction relative to the longitudinal axis (5).

6. A system for preparing tissue samples for histological investigations, the system comprising:
at least one of a stainer and a coverslipper having respective rack drawers;
a rack (1) configured to be received by the respective rack drawers for carrying specimen slides (4) through said at least one of a stainer and a coverslipper, the rack (1) having a longitudinal axis (5); and
a rack receptacle (13) configured to insertably receive a portion of the rack basket carrying the specimen slides (4) such that the longitudinal axis (5) of the rack (1) is disposed within said rack receptacle (13), the longitudinal axis (5) of the rack (1) being oriented horizontally in a first position and the specimen slides (4) in the rack (1) are arranged vertically next to one another relative to said longitudinal axis (5) of the rack (1), and the rack receptacle is pivotable around a rotation axis (8) into a second position in which the longitudinal axis (5) of the rack (1) is oriented vertically such that the specimen slides (4) are arranged horizontally next to one another relative to said longitudinal axis (5) and arranged such that the specimen slides (4) can be positioned into the coverslipper to receive coverslips;
wherein the rotation axis (8) extends obliquely with respect to the longitudinal axis (5) of the horizontally oriented rack (1), so that, the rack (1) can be pivoted back and forth between the first and the second position by means of a 180-degree rotation around the rotation axis (8);
wherein in the first position, the specimen slides (4) are slidably removable vertically relative to the longitudinal axis (5), and in the second position, the specimen slides (4) are slidably removable in a horizontal direction relative to the longitudinal axis (5).

7. The system according to claim 6, further comprising a base element (10) including a drive system (12), wherein the rack receptacle (13) is connected rotatably to the base element (10), and the drive system (12) is operable to rotate the rack receptacle (13) around the rotation axis (8).

8. A method for preparing tissue samples for histological investigations, the method comprising the step of:
immersing the rack carrying specimen slides into stain containers;
orienting the rack carrying specimen slides into a first position such that a longitudinal axis of the rack extends horizontally and in which specimen slides in the rack are arranged vertically next to one another relative to a longitudinal axis of the rack;
allowing stain from the stain containers to runoff the specimen slides from the first position;
sliding the rack into a rack receptacle;
pivoting the rack between the first position, and a second position in which the longitudinal axis of the rack extends vertically such that the specimen slides are arranged vertically next to one another relative to said longitudinal axis with a drive system attached to the rack receptacle;
moving the specimen slides from the rack in the second position to a coverslipping unit;
wherein the rack is pivoted 180 degrees from the first position into the second position and from the second position into the first position, around a rotation axis that extends obliquely with respect to the longitudinal axis of the horizontally oriented rack.

9. The rack turner according to claim 1, wherein the rack receptacle is configured to surround at least three sides of the rack basket when insertably received by the rack receptacle (13).

10. The rack turner according to claim 9, wherein the rack receptacle is configured to not contact the rack bail when insertably received by the rack receptacle (13).

11. The rack turner according to claim 10, wherein the rack bail is rotatable relative to the rack basket.

12. The rack turner according to claim 11, wherein the rack bail is configured to prohibit removal of the specimen slides from the rack basket when rotated into a first position, and permits removal of the specimen slides from the rack basket when rotated into a second position.

13. The rack turner according to claim 5, wherein the rack receptacle is spaced above a mounting surface in which the base element is mounted to.

14. The rack turner according to claim 13, wherein the base element is rotatably connected to a bottom corner of the rack receptacle.

15. The rack turner according to claim 14, wherein the bottom corner is a wall that is in contact with the rack bail when the rack is received by the base element.

* * * * *